US00PP20904P2

(12) United States Plant Patent
Michalik

(10) Patent No.: US PP20,904 P2
(45) Date of Patent: Mar. 30, 2010

(54) *GERANIUM* PLANT NAMED 'PACCHY'

(50) Latin Name: *Pelargonium×hortorum*
Varietal Denomination: Pacchy

(75) Inventor: Andrea Michalik, Dresden (DE)

(73) Assignee: Elsner PAC Jungpflanzen GbR, Dresden (DE)

( * ) Notice: Subject to any disclaimer, the term of this patent is extended or adjusted under 35 U.S.C. 154(b) by 0 days.

(21) Appl. No.: 12/291,557

(22) Filed: Nov. 12, 2008

(51) Int. Cl.
*A01H 5/00* (2006.01)

(52) U.S. Cl. ..... Plt./329

(58) Field of Classification Search ..... Plt./329
See application file for complete search history.

*Primary Examiner*—Susan B McCormick Ewoldt
(74) *Attorney, Agent, or Firm*—C. A. Whealy

(57) ABSTRACT

A new and distinct cultivar of Zonal *Geranium* plant named 'Pacchy', characterized by its compact, upright and rounded plant habit; freely branching habit; moderately vigorous growth habit; dark green-colored leaves; freely and early flowering habit; semi-double red purple-colored flowers; and good garden performance.

1 Drawing Sheet

Botanical designation: *Pelargonium×hortorum.*
Cultivar denomination: 'Pacchy'.

BACKGROUND OF THE INVENTION

The present invention relates to a new and distinct cultivar of Zonal *Geranium* plant, botanically known as *Pelargonium×hortorum,* and hereinafter referred to by the name 'Pacchy'.

The new Zonal *Geranium* plant is a product of a planned breeding program conducted by the Inventor in Dresden, Germany. The objective of the breeding program is to create new compact semi-double flowered Zonal *Geranium* cultivars with uniform plant habit, dark green-colored foliage and attractive flower coloration.

The new Zonal *Geranium* plant originated from a cross-pollination made by the Inventor in Dresden, Germany during the summer of 2003 of two unnamed proprietary selections of *Pelargonium×hortorum,* not patented. The new Zonal *Geranium* plant was discovered and selected by the Inventor as a single flowering plant from within the progeny of the stated cross-pollination in a controlled greenhouse environment in Dresden, Germany in June, 2004.

Asexual reproduction of the new Zonal *Geranium* plant by vegetative terminal cuttings in a controlled greenhouse environment in Dresden, Germany since December, 2004, has shown that the unique features of this new Zonal *Geranium* plant are stable and reproduced true to type in successive generations.

SUMMARY OF THE INVENTION

Plants of the new Zonal *Geranium* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Pacchy'. These characteristics in combination distinguish 'Pacchy' as a new and distinct cultivar of Zonal *Geranium:*

1. Compact, upright and rounded plant habit.
2. Freely branching habit.
3. Moderately vigorous growth habit.
4. Dark green-colored leaves.
5. Freely and early flowering habit.
6. Semi-double red purple-colored flowers.
7. Good garden performance.

Plants of the new Zonal *Geranium* differ primarily from plants of the parent selections in plant vigor and flower color.

Plants of the new Zonal *Geranium* can be compared to plants of *Pelargonium×hortorum* 'Pactwo', disclosed in U.S. Plant Pat. No. 13,234. In side-by-side comparisons conducted in Dresden, Germany, plants of the new Zonal *Geranium* differed from plants of 'Pactwo' in the following characteristics:

1. Plants of the new Zonal *Geranium* were more compact than plants of 'Pactwo'.
2. Plants of the new Zonal *Geranium* had shorter internodes than plants of 'Pactwo'.
3. Plants of the new Zonal *Geranium* had slightly smaller leaves than plants of 'Pactwo'.
4. Leaves of plants of the new Zonal *Geranium* did not have a discernible zonation pattern whereas plants of 'Pactwo' had a discernible leaf zonation pattern.
5. Plants of the new Zonal *Geranium* flowered earlier than plants of 'Pactwo'.
6. Plants of the new Zonal *Geranium* had smaller umbels with fewer flowers per umbel than plants of 'Pactwo'.
7. Plants of the new Zonal *Geranium* had larger flowers than plants of 'Pactwo'.

BRIEF DESCRIPTION OF THE PHOTOGRAPH

The accompanying colored photograph illustrates the overall appearance of the new Zonal *Geranium* plant, showing the colors as true as it is reasonably possible to obtain in colored reproductions of this type. Colors in the photograph may differ slightly from the color values cited in the detailed botanical description which accurately describe the colors of the new Zonal *Geranium* plant. The photograph comprises a side perspective view of a typical flowering plant of 'Pacchy' grown in a container.

DETAILED BOTANICAL DESCRIPTION

The aforementioned photograph and following observations, measurements and values describe plants grown in Dresden, Germany in a glass-covered greenhouse during the autumn and winter and under conditions which closely approximate commercial *Geranium* production. During the production of the plants, day temperatures averaged 18° C., night temperatures averaged 16° C. and light levels ranged from 15 kilolux to 100 kilolux. Plants were nine months from planting when the photograph and description were taken. In the detailed description, color references are made to The Royal Horticultural Society Colour Chart, 1995 Edition, except where general terms of ordinary dictionary significance are used.

Botanical classification: *Pelargonium×hortorum* 'Pacchy'.

Parentage:

*Female, or seed, parent.*—Unnamed proprietary selection of *Pelargonium×hortorum*, not patented.

*Male or pollen parent.*—Unnamed proprietary selection of *Pelargonium×hortorum,* not patented.

Propagation:

*Type.*—By vegetative terminal cuttings.

*Time to initiate roots, summer.*—About 18 days at temperatures of 20° C.

*Time to initiate roots, winter.*—About 22 days at temperatures of 20° C.

*Time to produce a rooted young plant, summer.*—About 25 days at temperatures of 20° C.

*Time to produce a rooted young plant, winter.*—About 30 days at temperatures of 20° C.

*Root description.*—Fine, fibrous; white in color.

*Rooting habit.*—Freely branching; dense.

Plant description:

*Plant/growth habit.*—Compact, upright to rounded plant habit; densely foliated; moderately vigorous growth habit. Freely basal branching habit with about ten lateral branches developing per plant.

*Plant height, to top of umbels.*—About 28 cm.

*Plant height, to top of leaves.*—About 15 cm.

*Plant width.*—About 40 cm.

*Lateral branches.*—Length: About 15 cm. Diameter: About 9 mm. Internode length: About 1 cm to 2 cm. Texture: Pubescent. Color: Close to 144A.

Foliage description:

*Arrangement.*—Alternate or opposite; simple.

*Length.*—About 4 cm.

*Width.*—About 6.5 cm.

*Shape.*—Reniform.

*Apex.*—Rounded.

*Base.*—Cordate.

*Margin.*—Bi-crenate.

*Venation pattern.*—Palmate.

*Texture, upper and lower surfaces.*—Pubescent; velvety.

*Color.*—Developing and fully expanded leaves, upper surface: Close to 137A; venation, close to 144A. Developing and fully expanded leaves, lower surface: Close to 137C; venation, close to 144A. Zonation pattern: Not discernible. Petiole: Length: About 3 cm to 5 cm. Diameter: About 2 mm. Texture, upper and lower surfaces: Pubescent. Color, upper and lower surfaces: Close to 144A.

Flower description:

*Flower arrangement.*—Semi-double rotate flowers arranged in rounded hemispherical umbels arising from apical leaf axils. Umbels displayed above the foliage on strong peduncles. Flowers face upright to outward; flowers slightly cupped. Flowers not fragrant.

*Quantity of flowers.*—Freely flowering habit; about 20 flower umbels per plant each with about 25 flower buds and open flowers.

*Time to flower.*—Early flowering habit, plants begin to flower about 65 days after planting.

*Flowering season.*—Year-round under greenhouse conditions. In the garden in Dresden, Germany, flowering is continuous from April until frost in the autumn.

*Flower longevity.*—Individual flowers last about six to ten days on the plant; umbels last about three to four weeks on the plant; flowers persistent.

*Umbel height.*—About 5 cm to 6 cm.

*Umbel diameter.*—About 8 cm to 10 cm.

*Flower diameter.*—About 4.5 cm to 5 cm.

*Flower depth* (*height*).—About 1 cm.

*Flower buds.*—Length: About 7 mm. Diameter: About 5 mm. Shape: Rounded. Color: Close to 144A.

*Petals.*—Quantity per flower: About eight; imbricate. Length: About 2.5 cm. Width: About 2.5 cm. Shape: Obovate. Apex: Rounded. Base: Attenuate. Margin: Entire. Texture, upper and lower surfaces: Smooth, glabrous; velvety. Color: When opening and fully opened, upper surface: Close to 57A; towards the base, close to 46A; at the base, close to 155D; venation, close to 45A. Color becoming closer to 45A with development. When opening and fully opened, lower surface: Close to 57B; at the base, close to 155D; venation, close to 66A.

*Petaloids.*—Quantity per flower: About two. Length: About 1.5 cm. Width: About 1 cm. Shape: Irregular. Apex: Rounded. Base: Attenuate. Margin: Entire. Texture, upper and lower surfaces: Smooth, glabrous; velvety. Color: When opening and fully opened, upper surface: Close to 57A; at the base, close to 155D; venation, close to 66A. Color becoming closer to 45A with development. When opening and fully opened, lower surface: Close to 57B; at the base, close to 155D; venation, close to 66A.

*Sepals.*—Quantity per flower: Five to six, arranged in a single whorl. Length: About 1 cm. Width: About 2 mm. Shape: Lanceolate. Apex: Acute. Margin: Entire. Texture, upper and lower surfaces: Pubescent. Color, upper and lower surfaces: Close to 144A; towards the base, close to 47A.

*Peduncle* (*umbel stem*).—Length: About 10 cm to 15 cm. Diameter: About 5 mm. Strength: Strong. Angle: Mostly erect. Texture: Pubescent. Color: Close to 144A.

*Pedicel* (*individual flower stem*).—Length: About 3 cm. Diameter: About 2 mm. Strength: Moderately strong; flexible. Texture: Pubescent. Color: Close to 59B.

*Reproductive organs.*—Androecium: Stamen quantity per flower: About eight to ten. Anther length: About 2 mm. Anther shape: Tubular. Anther color: Close to 172A. Pollen amount: Abundant. Pollen color: Close to 169C. Gynoecium: Pistil quantity per flower: One. Pistil length: About 1 cm. Stigma shape: Five to six-parted. Stigma color: Close to 46A. Style length: About 3 mm. Style color: Close to 47B. Ovary color: Close to 148B.

*Seeds.*—Shape: Elliptic. Length: About 3 mm. Diameter: About 1 mm. Color: Close to 165A.

Disease/pest resistance: Plants of the new Zonal *Geranium* have not been observed to be resistant to pathogens and pests common to Zonal *Geraniums*.

Garden performance: Plants of the new Zonal *Geranium* have been observed to tolerate rain, wind and temperatures ranging from about 0° C. to about 35° C. to 40° C. and have demonstrated good garden performance.

It is claimed:

1. A new and distinct Zonal *Geranium* plant named 'Pacchy' as illustrated and described.

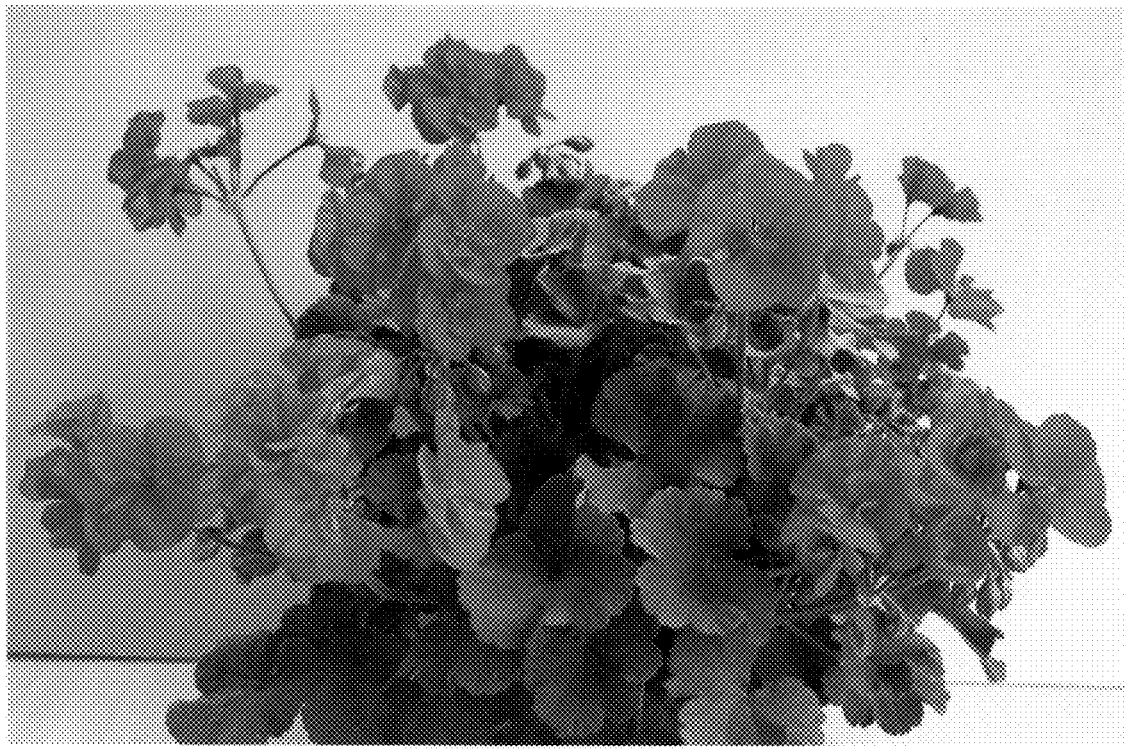

* * * * *